United States Patent

Mills

Patent Number: 6,074,376
Date of Patent: *Jun. 13, 2000

[54] ABSORBENT ARTICLE WRAPPER COMPRISING SIDE FLAP FASTENER COVER

[75] Inventor: Sue Ann Mills, Cincinnati, Ohio

[73] Assignee: The Procter & Gamble Company, Cincinnati, Ohio

[*] Notice: Under 35 U.S.C. 154(b), the term of this patent shall be extended for 436 days.

[21] Appl. No.: 08/831,036

[22] Filed: Apr. 1, 1997

Related U.S. Application Data

[63] Continuation of application No. 08/547,210, Oct. 24, 1995, abandoned, which is a continuation-in-part of application No. 08/380,769, Jan. 20, 1995, abandoned.

[51] Int. Cl.[7] .............................. A61F 13/15; A61B 17/06
[52] U.S. Cl. .................. 604/390; 604/385.1; 604/387; 206/438
[58] Field of Search ................................. 604/385.1–390; 206/438–440

[56] References Cited

U.S. PATENT DOCUMENTS

| | | |
|---|---|---|
| H1454 | 1/1995 | Cucuzza et al. . |
| 4,556,146 | 12/1985 | Swanson et al. . |
| 4,608,047 | 8/1986 | Mattingly . |
| 4,701,178 | 10/1987 | Glaug et al. . |
| 4,759,754 | 7/1988 | Korpman . |
| 5,088,993 | 2/1992 | Gaur . |
| 5,330,461 | 7/1994 | Leeker ..................................... 604/389 |
| 5,391,160 | 2/1995 | Runeman et al. . |
| 5,413,568 | 5/1995 | Roach et al. . |
| 5,462,166 | 10/1995 | Minton et al. . |
| 5,484,636 | 1/1996 | Berg, Jr. et al. . |
| 5,520,676 | 5/1996 | Lavash et al. ............................ 604/389 |
| 5,683,377 | 11/1997 | Mizutani . |

FOREIGN PATENT DOCUMENTS

| | | |
|---|---|---|
| 0 299 532 | 1/1989 | European Pat. Off. . |
| 0 749 742 | 12/1996 | European Pat. Off. . |
| 6-75446 | 10/1994 | Japan . |
| 05108275 | 11/1994 | Japan . |
| 6315504 | 11/1994 | Japan ...................................... 604/389 |
| 7-39820 | 7/1995 | Japan . |
| WO 91/16873 | 11/1991 | WIPO . |
| WO 91/18574 | 12/1991 | WIPO . |
| 93/09743 | 5/1993 | WIPO ..................................... 604/389 |
| 93/20790 | 10/1993 | WIPO ..................................... 604/389 |
| 94/27540 | 12/1994 | WIPO ..................................... 604/390 |
| WO 97/16143 | 5/1997 | WIPO . |

*Primary Examiner*—John G. Weiss
*Assistant Examiner*—Dennis Ruhl
*Attorney, Agent, or Firm*—Matthew P. Fitzpatrick; Jeffrey V. Bamber

[57] ABSTRACT

An individually packaged absorbent article having side flaps with fasteners, such as adhesive fasteners thereon, is disclosed. The wrapper for individual packaging the absorbent article has a flap adhesive cover joined thereto. The flap adhesive cover protects the fasteners located on the side flaps of the absorbent article and maintains the flaps in a position which protects an absorbent side of the absorbent article from contamination until the article is ready for use. The wrapper overlays one major surface of the absorbent article and by folding the article and sealing the wrapper in that folded orientation, an individually packaged disposable absorbent article is provided.

12 Claims, 7 Drawing Sheets

ABSORBENT ARTICLE WRAPPER COMPRISING SIDE FLAP FASTENER COVER

This is a continuation of application Ser. No. 08/547,210, filed on Oct. 24, 1995 now abandoned, which is a continuation-in-part of application Ser. No. 08/380,769, filed Jan. 20, 1995 and now abandoned.

FIELD OF INVENTION

The present invention relates generally to absorbent articles such as sanitary napkins, panty liners, adult incontinence pads, and the like which have side flaps. The present invention provides a wrapper for individually wrapping the absorbent articles and a cover for protecting an attachment means on the flaps of the absorbent article.

BACKGROUND OF THE INVENTION

All manner and variety of absorbent articles configured for the absorption of body fluids such as menses, urine and feces are well known. Absorbent articles, particularly sanitary napkins, having wings or flaps are disclosed in the literature and are available in the marketplace.

Generally, the flaps of such absorbent articles extend laterally from a central absorbent means and are intended to be folded around the edges of a wearer's undergarment in the crotch region. Thus, in use the flaps are disposed between the edges of the wearer's undergarment in the crotch region and the wearer's thighs. Commonly, the flaps are provided with an attachment means for affixing the flaps to the underside of the wearer's undergarment. The flaps serve at least two purposes. First, the flaps prevent exudates which otherwise would soil the edges of the wearer's undergarment from doing such. Second, the flaps help stabilize the napkin from shifting out of the position chosen by the wearer. This is especially so when the flaps are affixed to the underside of the undergarment.

Sanitary napkins having flaps of the various types are disclosed in U.S. Pat. No. 4,687,478, entitled "Shaped Sanitary Napkin With Flaps," which issued to Van Tilburg on Aug. 18, 1987, U.S. Pat. No. B1 4,589,876, entitled "Sanitary Napkin," which issued to Van Tilburg on May 20, 1986 and U.S. Pat. No. 5,389,094 entitled "Absorbent Article Having Flaps and Zones of Differential Extensibility," which issued to Lavash et al. on Feb. 14, 1995.

While there are a great many variations in the specific structural features of absorbent articles, they are frequently presented to the consumer in the same manner. Essentially, the absorbent article, irrespective of what specific structural features are used, is packaged in a box or bag from which the consumer withdraws the ready-to-use articles as needed. If the consumer needs only one article for later use, the consumer must take precautions to protect the article from soiling or contamination from the time it is removed from the box or bag until the article is used. This is a particular problem with respect to catamenial pads. For example, if a woman wishes to carry a catamenial pad with her for use away from home, she would have to take precautions to insure that the pad was not damaged or soiled when carried in her purse or pocket.

The protection of individual absorbent articles has been addressed in the prior art. Bandages, for example, are commonly packaged individually and sold to the consumer in some sort of container which holds a convenient number of the individually packaged articles. Catamenial pads have likewise been individually packaged and sold to the consumer in a container holding a convenient number of the individually packaged articles. U.S. Pat. No. 2,750,033 entitled "Napkin Packaging" which issued to J. B. Pickens on Jun. 12, 1956 and U.S. Pat. No. 3,973,567 entitled "Wrapped Sanitary Napkins" which issued to S. S. Srinivasan et al. on Aug. 10, 1976 disclose examples of individually packaged sanitary napkins. Although these wrappers protect the enclosed sanitary napkin, they require a quantity of wrapper material which is sufficient to cover the entire surface area of each napkin when it is exposed in a fully open position.

Other attempts at protecting individual absorbent articles have reduced the quantity of wrapper material required for the protection of each absorbent article. Notably, U.S. Pat. No. 4,556,146 entitled "Individually Packaged Disposable Absorbent Article" which issued to Swanson et al. on Dec. 3, 1985 and U.S. Pat. No. 5,088,993 entitled "Sanitary Napkin with Individual Self Wrapping Means" which issued to Gaur on Feb. 18, 1992 disclose examples of individually packaged catamenial pads which require wrapping material sufficient to cover only one major surface (i.e. either the body facing side or the garment facing side) of the sanitary napkin and material sufficient to extend a distance beyond each edge of that one major surface to allow protection of the sanitary napkin in a folded position. These publications, however, do not disclose arrangements for packaging absorbent articles having flaps.

The flaps of such sanitary napkins may be folded to conserve space during packaging, i.e., the period between manufacture of the sanitary napkin and its intended first use by the wearer. At the time of the first use by the wearer, the flaps are usually unfolded to facilitate installation of the sanitary napkin into the wearer's undergarment. Consequently, when the wearer installs the sanitary napkin into the undergarment, the sanitary napkin is typically in the wearing position, with the topsheet facing the wearer, while the wearer manipulates the flaps and any associated protective adhesive cover (or release strip). There can be an inconvenience associated with manipulating flaps and any associated release strip when the flaps are folded over the backsheet. Flaps folded over the backsheet are behind and obscured by the sanitary napkin, so that the flaps cannot be seen while the wearer is attempting to install the sanitary napkin to the undergarment. Also, flaps folded over the backsheet may have a tendency to become adhered to the adhesive fastener on the backsheet, unless held apart. Furthermore, such configuration leaves the body facing surface open to contamination.

Problems arise with the traditional means for protecting such attachment means of an absorbent article's flaps, such as protective strips. Problems arise with the care that must be taken when removing these protective strips so that the flaps do not inadvertently adhere to each other or another part of the product as the protective strips are being removed. The user must, therefore, carefully handle the absorbent article when removing the protective strips. Additionally, the user must then properly dispose of the various protective strips to prevent them from becoming litter.

Other attempts to protect the attachment means of the flaps such as U.S. Pat. No. 4,701,178 entitled "Sanitary Napkins with Flaps" which issued to Glaug et al. on Oct. 20, 1987, have incorporated the protective strips of the flaps with a protective strip used to cover the adhesive that secures the main body of a sanitary napkin to the wearer's undergarment. Problems arise with this configuration in that the wearer must take care not to damage the flaps or tear the protective strip when removing the protective strip from the sanitary napkin. Additionally, the typical problems with having flaps in a backsheet facing orientation (as discussed above) are experienced with this configuration.

Therefore, a primary object of the present invention is to provide an individual wrapper for an individual absorbent article that has flaps which have fasteners thereon wherein the wrapper overlays only one major surface of the absorbent article and covers the fasteners on the absorbent article's flaps.

It is another object of the present invention to provide a wrapper for an individual absorbent article that has flaps having fasteners thereon, wherein the function of all protective elements for the fasteners are incorporated into the wrapper of the absorbent article.

It is another object of the present invention to provide a wrapper for an individual absorbent article that has flaps having fasteners thereon, wherein the wrapper is comprised of a single piece.

It is another object of the present invention to provide a wrapper for an individual absorbent article that has flaps having fasteners thereon, wherein the wrapper is configured to protect flap attachment means which are folded over the body facing topsheet of the absorbent article when the central pad adhesive element can be attached to the wearer's undergarment.

It is another object of the present invention to provide a wrapper for an individual absorbent article that has flaps employing attachment means, wherein the wrapper and all protective elements may be removed from the absorbent article with one motion.

These and other objects of the present invention will be more readily apparent when considered in reference to the following description and when taken in conjunction with the accompanying drawings.

SUMMARY OF THE INVENTION

The present invention provides a wrapper for individually wrapping an absorbent article such as a sanitary napkin which has flaps that have an attachment means, such as adhesive fasteners thereon. The wrapper has a flap adhesive cover or flap release element joined thereto for protecting the adhesive patches of said flaps when said flaps are folded over the topsheet of the sanitary napkin. The wrapper comprises a main wrapper sheet that preferably only overlays the backsheet of the sanitary napkin and extends slightly beyond the perimeter of the sanitary napkin. In a preferred embodiment, the flap release element is joined at one end to one longitudinal end of the main wrapper sheet and extends to a free end which overlays a portion of the topsheet of the sanitary napkin so that the flap release element attaches to the adhesive patches of the flaps when the flaps are folded over the topsheet.

To wrap an individual absorbent article with the wrapper of the present invention, the sanitary napkin is placed garment-facing side down on the main wrapper sheet so that the adhesive on the garment-facing side of the sanitary napkin overlies the main wrapper sheet. The flaps are then folded over the topsheet so that the adhesive patches on the garment-facing side of the flaps are exposed. The flap adhesive cover is then positioned on top of the flap adhesive patches and a first end region of the wrapper and the portion of the sanitary napkin associated therewith are folded inward over the central portion of the sanitary napkin. The opposing end region of the disposable wrapper and the portion of said sanitary napkin associated therewith are then folded as a unit atop the first end region. The longitudinal sides of the wrapper are frangibly sealed to provide the individually packaged absorbent article and the wrapper is preferably releasably retained in its folded configuration with an adhesive tape tab.

The wrapper and release strip of the present invention provide less expensive packaging of an absorbent article. Also, they provide an individual package for an absorbent article having flaps wherein all elements required for packaging are joined as a single unit to prevent excess litter. They further allow easy placement of the absorbent article in an undergarment while the topsheet and flap adhesive of the absorbent article remain protected from contamination. The wrapper and release strip can also allow a single motion detachment of the wrapper and all associated adhesive release strips from the absorbent article.

DETAILED DESCRIPTION OF THE INVENTION

Figure 1:
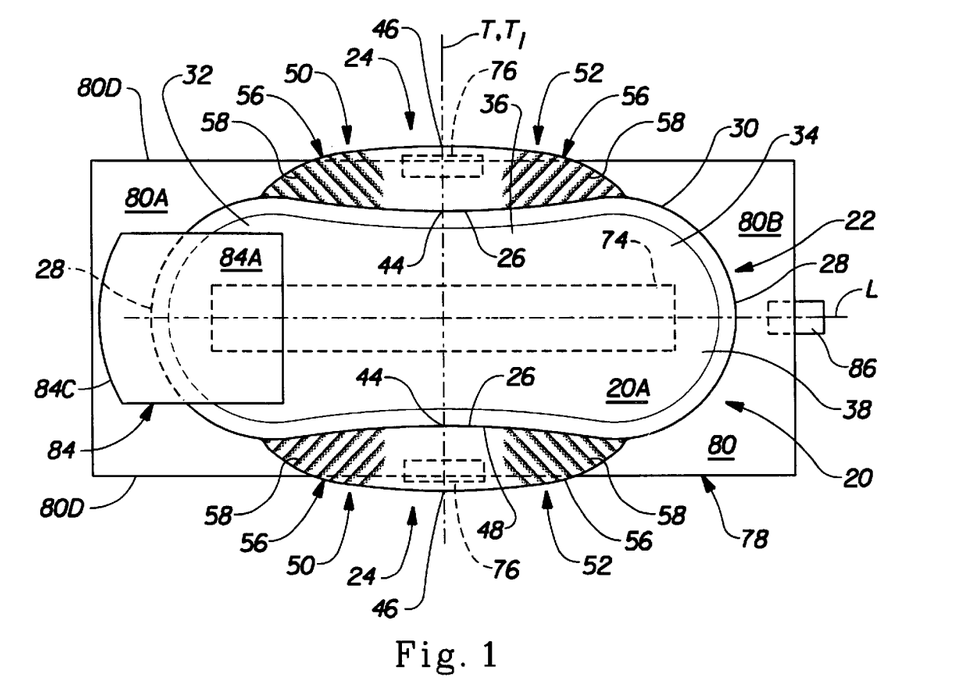
FIG. 1 is a top plan view of a preferred embodiment of the wrapper of the present invention in an opened position with a preferred sanitary napkin disposed thereon and the flaps of the sanitary napkin outstretched.
Figure 2:
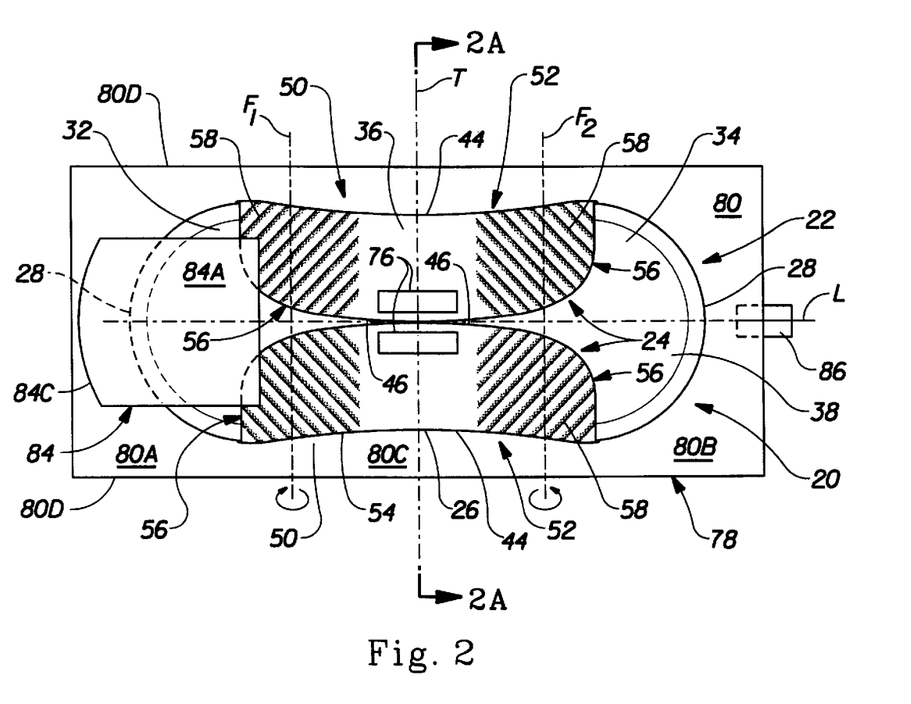
FIG. 2 is a top plan view of the wrapper of the present invention shown in FIG. 1 with the flaps of the sanitary napkin folded over the topsheet.
Figure 2A:
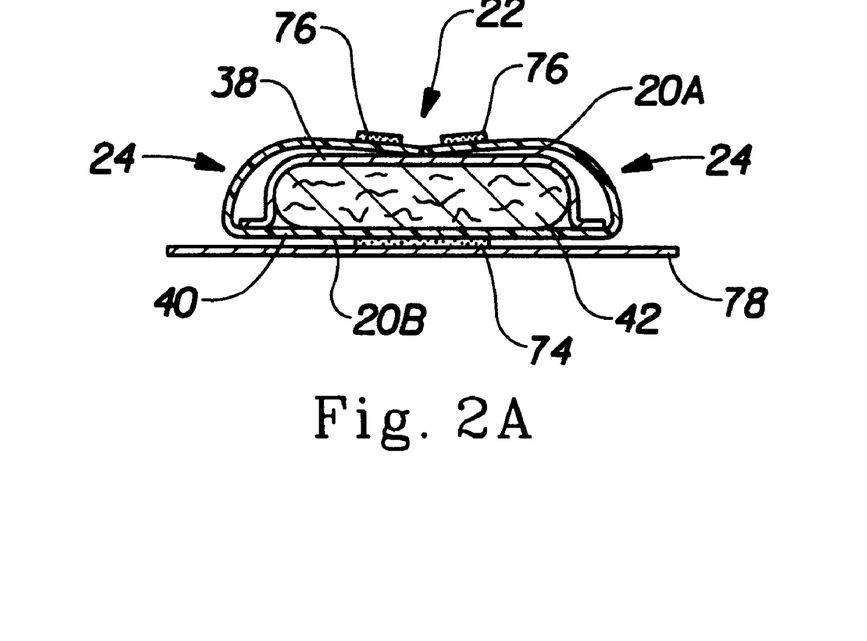
FIG. 2A is a cross-sectional view of FIG. 2 taken along the transverse centerline T.

Referring now to the drawings, the present invention is embodied in a preferred but non-limiting embodiment. As shown in FIGS. 1, 2, and 2A, the invention comprises a wrapper 78 for a disposable absorbent article, particularly a sanitary napkin 20.

The sanitary napkin 20 is used to collect vaginal discharges, such as menses, and prevent soiling of the wearer's clothing by such discharges. As shown in FIG. 2A, the sanitary napkin 20 basically comprises a main body portion 22 and two flaps 24. The main body portion 22 of the sanitary napkin 20 may have a fastener, such as a pressure sensitive adhesive fastener 74 thereon for fastening the main body portion 22 in the wearer's undergarment. The flaps 24 preferably each have fasteners thereon, such as a pressure sensitive adhesive fastener 76, for releasably affixing the flaps 24 of the sanitary napkin 20 in a configuration folded around the edges of the crotch of the wearer's undergarment. The wrapper 78 of the present invention serves to cover and protect the flap fasteners 76, the main body fastener (if there is one), and is folded around the sanitary napkin 20 to provide an individual package for the sanitary napkin 20. Before looking at the characteristics of the wrapper 78 in greater detail, the properties of the sanitary napkin 20 will be briefly discussed.

The sanitary napkin 20 (and the main body portion 22 thereof) has two surfaces, a liquid pervious body-contacting surface or "body surface" 20A that is intended to be worn adjacent to the body of the wearer, and a liquid impervious garment surface 20B. The sanitary napkin 20 is shown in FIG. 1 as viewed from its body surface 20A. The sanitary napkin 20 has two centerlines, a principal longitudinal centerline L and a principal transverse centerline T. The term "longitudinal," as used herein, refers to a line, axis or direction in the plane of the sanitary napkin 20 that is generally aligned with (e.g. approximately parallel to) a vertical plane which bisects a standing wearer into left and right body halves when the sanitary napkin 20 is worn. The terms "transverse," "lateral" or "width" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 also has two end regions, which are designated first end region 32 and second end region 34. A central region 36 is disposed between the end regions 32 and 34. The end regions 32 and 34 extend outwardly in the longitudinal direction from the edges of the central region 36 about ⅛ to about ⅓ of the length of the main body portion. A detailed description of the characteristics of a central region and two end regions for a sanitary napkin is contained in U.S. Pat. No. 4,690,680 issued to Higgins on Sep. 1, 1987.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the wrapper of the present invention is not limited to use with absorbent articles of the type or having the specific configurations shown in the drawings.

FIG. 2A shows the individual components of the main body portion 22 of the sanitary napkin 20. The main body portion 22 of the sanitary napkin preferably comprises at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations).

Suitable materials for the components of the main body portion 22, and some of the various configurations in which such components can be assembled are described generally in U.S. Pat. No. 4,321,924, entitled "Bordered Disposable Absorbent Article" issued to Ahr on Mar. 30, 1982; U.S. Pat. No. 4,425,130, entitled "Compound Sanitary Napkin" issued to DesMarais on Jan. 10, 1984; U.S. Pat. No. 4,950, 264, entitled "Thin, Flexible Sanitary Napkin" issued to Osborn on Aug. 21, 1990: U.S. Pat. No. 5,308,346, entitled "Elasticized Sanitary Napkin" issued to Sneller, et al. on May 3, 1994; and U.S. Pat. No. 5,389,094, entitled "Absorbent Article Having Flaps and Zones of Differential Extensibility" issued to Lavash, et al. on Feb. 14, 1995. The main body portion 22 of the sanitary napkin may also be comprised of one or more extensible components such as those sanitary napkins, and the like described in U.S. patent application Ser. Nos. 07/915,133 and 07/915,284, both filed Jul. 23, 1992, in the name of Osborn, et al. (PCT Publication Nos. WO 93/01785 and 93/01786, both published Feb. 4, 1993).

FIGS. 1–2A show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42 and the backsheet 40 is preferably joined to the garment-facing side of the absorbent core. The topsheet 38 and backsheet 40 can be joined to the absorbent core in any suitable manner known in the art for this purpose, such as by an open pattern of adhesives. The portions of the topsheet 38 and backsheet 40 that extend beyond the edges of the absorbent core are preferably also joined to each other. These portions of the topsheet 38 and backsheet 40 can also be joined in any suitable manner known in the art. Preferably, in the embodiment shown, these portions of the topsheet 38 and backsheet 40 are joined using adhesives over substantially the entire portions that extend beyond the edges of the absorbent core 42, and a crimp seal around the periphery 30 of the main body portion 22 where the topsheet 38 and backsheet 40 are densified by the application of pressure or heat and pressure.

The sanitary napkin 20 shown in FIGS. 1–2A, as discussed above, also comprises a pair of flaps 24 that are joined to the main body portion 22. The flaps 24 extend laterally outward beyond the longitudinal side edges 26 of the main body portion 22 from their proximal edges 44 to their distal edges (or "free ends") 46. The flaps 24 extend outward from at least the central region 36 of the main body portion 22. As shown in FIG. 1, each flap 24 is divided into a front half 50, and a back half 52 by a flap transverse centerline $T_1$. The flap transverse centerline $T_1$ may coincide with the principal transverse centerline T of the sanitary napkin, but this is not absolutely required.

The flaps 24 can be joined to the main body portion 22 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–2A, the flaps 24 are integral with the main body portion 22 (that is, the flaps 24 comprise integral extensions of the topsheet 38 and backsheet 40).

In other alternative embodiments, the flaps 24 can comprise one or more separate components that are joined to the garment-facing side of the main body portion 22. Preferably, in such a case, the flaps 24 each comprise a separate component that is joined to the garment-facing side of the main body portion 22. In such alternative embodiments, the flaps 24 are preferably otherwise unattached to the garment-facing side of the main body portion 22 of the sanitary napkin 20 between the points where they are attached to the main body portion and the longitudinal side edges 26 of the main body portion. The flaps 24 in these latter embodiments can be joined to the garment-facing side of the main body portion 22 by any suitable attachment mechanism. Suitable attachment mechanisms include, but are not limited to adhesives, and the like.

The places or regions on the sanitary napkin 20 where the flaps 24 are joined to (or extend from) the main body portion 22, are referred to herein as "junctures". These regions will typically be longitudinally-oriented (or "longitudinal") junctures, such as lines of juncture 48. These regions can be any of various curved or straight lines, but they are not limited to lines. Thus, the junctures can comprise flanges, strips, intermittent lines, and the like.

The flaps 24 may be of any configuration desired, with one preferred configuration being shown in FIG. 1. FIG. 1 shows that the flaps 24 are provided with zones of extensibility (or "zones of differential extensibility") 56 in the front half 50 and the back half 52 of each flap 24. The zones of extensibility 56 relieve stresses which are created in flaps 24 by the folding of the flaps 24 around the crotch of the wearer's undergarment. The zones of extensibility 56 thereby help eliminate bunching of flaps 24 caused by said stresses. Preferably, in the embodiment shown in FIG. 1, the zones of extensibility 56 comprise pre-corrugated or "ring rolled" regions of the flaps 24 in which the corrugations 58 define ridges and valleys that are oriented at an angle to the principal longitudinal centerline, L. Suitable structures for providing the flaps 24 with zones of extensibility 56 are described in greater detail in U.S. Pat. No. 5,389,094 issued to Lavash, et al. and in commonly assigned copending U.S. patent application Ser. No. 08/380,769, entitled "Absorbent Article Having Flaps With Gathered Portions" filed in the name of Sue A. Mills, et al. on Jan. 30, 1995.

The sanitary napkin 20 preferably also has fasteners for securing the sanitary napkin 20 in place in a wearer's undergarment. FIGS. 1 and 2 show a preferred arrangement of fasteners which comprises a main body portion (or central pad) fastener, such as central pad adhesive 74, and flap fasteners, such as flap adhesives 76. The fasteners used with the sanitary napkin 20 are not limited to adhesive fasteners. Any suitable type of fastener known in the art can be used for this purpose, however. For example, the sanitary napkin 20 could be secured in place in a wearer's undergarment by mechanical fasteners, such as VELCRO®, or by a combination of adhesive and mechanical fasteners. For simplicity, however, the fasteners will be described in terms of adhesive fasteners and these fasteners are preferably pressure sensitive adhesive fasteners. Suitable pressure sensitive adhesive fasteners are described in greater detail in U.S. Pat. No. 4,917,697.

The central pad adhesive 74 and flap adhesives 76 can be provided in any suitable configuration. In the preferred embodiment shown, the central pad adhesive 74 is provided in the form of a longitudinally oriented strip of adhesive that is centered about the principal longitudinal centerline L. The flap adhesives 76 are provided in the form of a generally rectangular patch of adhesive on each flap 24. The central pad adhesive 74 provides an adhesive attachment means for securing the main body portion 22 of the sanitary napkin in the crotch portion of a panty. The flap adhesive patches 76 are used to assist in maintaining the flaps 24 in position after they are wrapped around the edges of the crotch portion of the panty. The flaps can be maintained in position by attaching the flaps 24 to the undergarment, or to the opposing flap.

FIGS. 1–2A show one preferred version of the wrapper 78 of the present invention. As shown in FIG. 1, the wrapper, generally designated by reference number 78 comprises several elements. These elements can comprise integral portions of a single member or article, or they can comprise separate components joined to a member or article. The elements comprising the wrapper 78 include: a main wrapper sheet 80; an optional release component, such as a release paper (or release coating) 82 disposed on one side of the main wrapper sheet 80; and a flap fastener cover, such as flap adhesive cover 84.

The main wrapper sheet 80 (or "wrapper sheet") is the portion of the wrapper 78 which will be folded around the sanitary napkin 20 to provide an individual package for the sanitary napkin 20. The main wrapper sheet 80 preferably covers and is releasably attached to the central pad fastener 74. The main wrapper sheet 80 preferably has dimensions that are slightly larger than those of the main body portion 22 of the sanitary napkin 20. Preferably, as shown in FIGS. 1 and 2, the main wrapper sheet 80 has longitudinal edge portions 80D which extend beyond the longitudinal edges 26 of the main body portion 22 of the sanitary napkin 20. The main wrapper sheet 80 preferably also has a first end portion 80A and a second end portion 80B which extend beyond the end edges 28 of the main body portion 22 of the sanitary napkin 20. It is recognized, however, that satisfactory protection of sanitary napkin 20 may be afforded by a wrapper which is not larger than the main body portion 22 of the sanitary napkin 20.

The main wrapper sheet 80 can be made from any suitable material. The main wrapper sheet 80 is preferably manufactured from a thin flexible material which is liquid impermeable so that the wrapper 78 will be suitable for wrapping and disposing of a used sanitary napkin 20. For example, polyethylene films have been found to work well.

The main wrapper sheet 80 can be provided with the optional release component, such as release paper (or release coating) 82 so that the main wrapper sheet 80 will release from the central pad fastener 74 when the wearer removes the sanitary napkin 20 from the wrapper 78. If a separate release paper is used, it can comprise any suitable material known in the art for this purpose, such as coated papers. Suitable release paper are described in U.S. Pat. No. 4,917,697. Such a release paper can be laminated to the inside surface of the main wrapper sheet 80. If a release coating is used, the coating can be applied directly to the inside surface of the main wrapper sheet 80. Such a coating can comprise any material known in the art for this purpose, with silicone coatings being preferred. If a coating is used, the coating 82 may be provided by coating only that zone of the main wrapper sheet 80 which will substantially contact the central pad adhesive 74. Alternatively, the entire inside surface of the main wrapper sheet 80 may be coated. Coating the entire inside of a wrapper is disclosed in U.S. Pat. No. 5,181,610 entitled "Flexible Container with Nonstick Interior" which issued to Quick et al. on Jan. 26, 1993.

The flap adhesive cover (or "flap release strip") 84 covers and protects the flap adhesives 76 and maintains the flaps 24 in position folded over the topsheet 38 for packaging. In the preferred embodiment shown in FIGS. 1 and 2, the flap adhesive cover 84 extends from the first end portion 80A of the main wrapper sheet 80. The flap adhesive cover 84 is preferably joined to the main wrapper sheet 80 and biased toward the main wrapper sheet 80 so that it will remain in the configuration shown in FIGS. 1 and 2. As shown in FIG. 1, the flap adhesive cover 84 is joined to main wrapper sheet 80 at fixed end 84C. The distal end 84D of the flap adhesive cover 84 extends toward central portion 80C of main wrapper sheet 80 and toward the central portion 36 of sanitary napkin 20. When the wrapper 78 is in the flat configuration shown in FIG. 1, the flap adhesive cover 84 lies over first end region 32 of sanitary napkin 20. The flap adhesive cover 84 can be of any suitable size and shape. Although the figures depict a flap adhesive cover 84 which is only of sufficient width (its dimension measured parallel to the transverse centerline T) to cover and protect the flap adhesives 76. A flap adhesive cover 84, which is of a width equal to the width of the main wrapper sheet 80 or any width therebetween is also contemplated herein.

Figure 3:
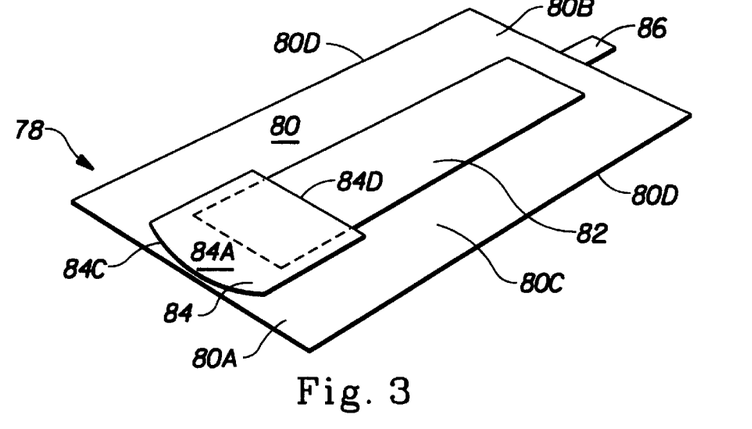
FIG. 3 is a perspective view of one preferred wrapper of the present invention.

The flap adhesive cover 84 has two faces, one of which is a non-stick face (or releasable face) 84A, which is capable of releasable attachment with the flap fasteners, and an opposite face or side 84B. Preferably, as shown in FIG. 3, the non-stick face 84A of the flap adhesive cover 84 faces away from the main wrapper sheet 80 so that it will be able to releasably adhere to the flap adhesive 76 when the sanitary napkin 20 and the wrapper 78 are in the folded configuration discussed below. When the flap fasteners 76 comprise adhesive fasteners, the non-stick face 84A can be provided by attaching a separate release paper or element to the flap adhesive cover 84 which is treated with a non-stick material, or by treating all or a portion of the the flap adhesive cover with a non-stick coating, such as by silicone coating a portion of the flap adhesive cover 84. Alternatively, if the flap fasteners 76 comprise mechanical fasteners, such as VELCRO® fasteners, the non-stick face may be provided by a nonwoven material capable of releasably engaging the mechanical fastening material. The opposing side 84B of flap adhesive cover 84 need not have, and preferably does not have, a release coating thereon. The opposing side 84B need not have a release coating since it will only be in contact with the topsheet 38 in first end region 32 of sanitary napkin 20 when the sanitary napkin 20 is disposed on wrapper 78 and placed in the folded configuration.

Figure 3A:
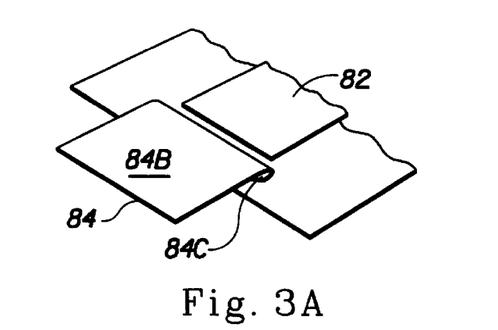
FIG. 3A is a fragmented perspective view of the wrapper shown in FIG. 3 with the free end of the flap release element folded back away from the main wrapper sheet.
Figure 3B:
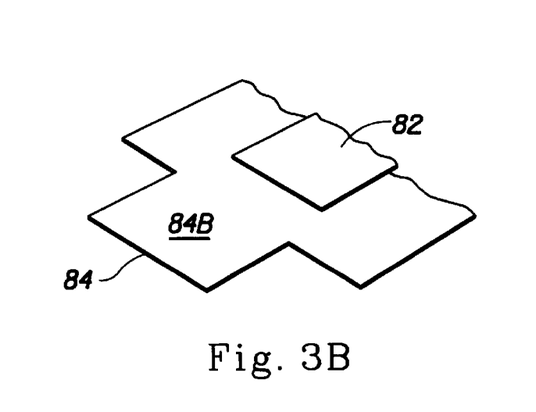
FIG. 3B is a fragmented perspective view of an alternative embodiment of the wrapper of the present invention.

FIG. 3B shows a variation of the flap adhesive cover 84 shown in the preceding drawing figures. In the embodiment shown in FIG. 3B, instead of being a separate component of the main wrapper sheet 80, the flap adhesive cover 84 is an integral portion of the main wrapper sheet 80.

The wrapper 78 preferably also comprises an optional package fastener 86 for retaining the package formed by folding the wrapper and sanitary napkin in its folded configuration. The package fastener 86 is preferably both releasably attachable to the package and resealable. The package fastener 86 may be comprised of any releasably attachable and resealable fastener known in the art, such as spots or patches of adhesive, tapes, and mechanical fasteners. A tape tab with a pressure sensitive adhesive located thereon has been found to work well. The package fastener 86 can be disposed at any suitable location on the wrapper 78. In the embodiment shown in FIGS. 1 and 2, the package fastener 86 is preferably positioned at opposing second end portion 80B of the main wrapper sheet 80.

Figure 2B:
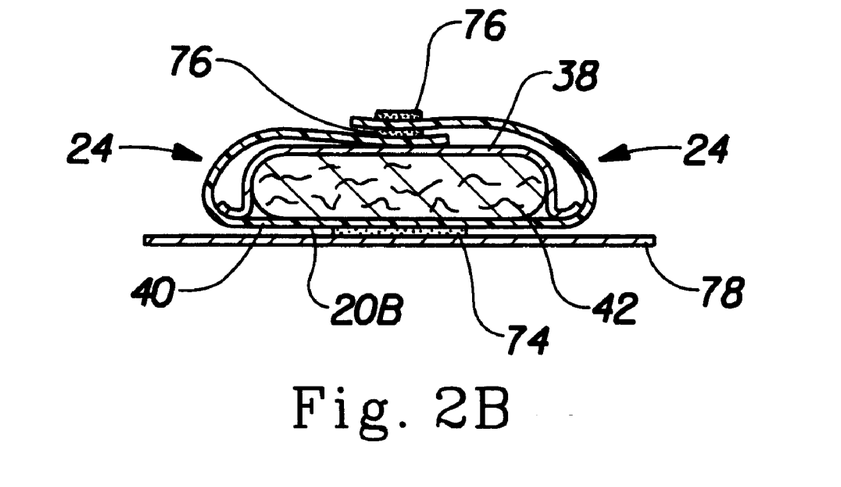
FIG. 2B is a cross-sectional view of an alternate embodiment of the flaps of the sanitary napkin in an alternative topsheet protecting position.

For the initial packaging of the sanitary napkin 20 in the wrapper 78, the garment-facing side 20B of the main body portion 22 is placed on top of the main wrapper sheet 80. The sanitary napkin 20 is positioned so that the central body fastener 74 lies over the release paper or release coating 82 on the main wrapper sheet 80. The flaps 24 are then preferably folded over the topsheet 38 so that the flaps 24 are in the configuration shown in FIGS. 2 and 2A. Folding the flaps 24 in the configuration shown in FIGS. 2 and 2A exposes the patches of adhesive 76 disposed on the garment-facing side of flaps 24 and causes the flaps 24 to cover at least a portion of the topsheet 38. Folding the flaps 24 over the topsheet 38 can, thus, be considered to provide a degree of protection to prevent the topsheet 38 from becoming soiled prior to use. In alternative embodiments, where one or both of the flaps 24 has a greater span (that is, its dimension measured in the transverse direction), the flaps 24 can be folded over the topsheet 38 so that one of the flaps 24 at least partially overlays the other flap 24 as shown in FIG. 2B. The second flap 24 overlays, attaches to, and protects the flap attachment means 76 of the first flap 24. The flap adhesive cover 84 will then overlay, attach to and protect the flap fastener 76 of the second flap 24.

After folding the flaps 24 over the topsheet 38, the sanitary napkin 20 and main wrapper sheet 80 will then preferably be folded into three sections that are defined by fold axes F1 and F2 shown in FIG. 2. The fold axes F1 and F2 will divide both the sanitary napkin 20 and the main wrapper sheet 80 into three sections. As shown in FIG. 2, the first and second end regions 32 and 34 of sanitary napkin 20 lie longitudinally outboard of the fold axes F1 and F2. The central region 36 of the sanitary napkin 20 lies between preferred fold axes F1 and F2. The first and second end portions, 80A and 80B, of main wrapper sheet 80 are separated at fold axes F1 and F2 by the central portion 80C of main wrapper sheet 80.

Figure 4:
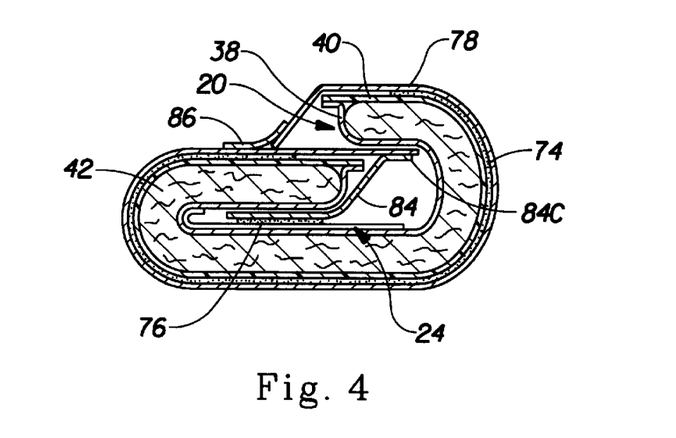
FIG. 4 is a cross-sectional view (taken along the longitudinal centerline) of one preferred wrapper of the present invention with a sanitary napkin therein in a folded configuration.
Figure 4A:
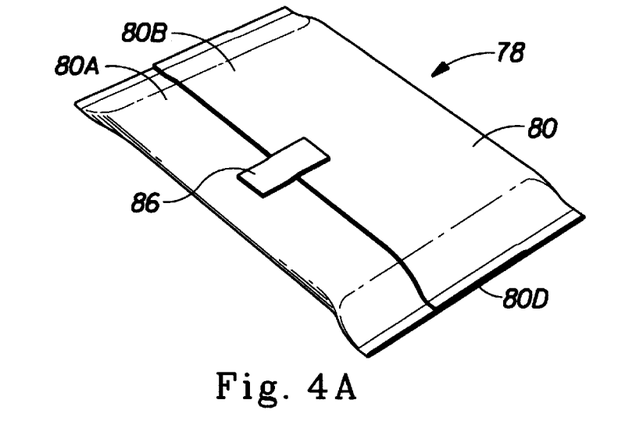
FIG. 4A is a view of a sanitary napkin and its associated wrapper after they have been folded and sealed.

FIG. 4 and FIG. 4A depict the package for the sanitary napkin formed by folding the wrapper 78 and sanitary napkin 20 in one preferred configuration for shipment, sale, and convenient carrying by the wearer. As shown in FIG. 4, the first end portion 80A of the main wrapper 80, along with the first end region 32 of the sanitary napkin 20, and the flap adhesive cover 84 are folded about first fold axis F1 onto the central region 36 of sanitary napkin 20. When the sanitary napkin 20 and wrapper 78 are folded in this manner, the nonstick face 84A of flap adhesive cover 84 is placed over the flap fasteners 76 and is releasably attached to each adhesive patch 76. In addition, the flap adhesive cover 84 provides a connection between each flap 24 that spans the flaps 24, thereby keeping the flaps 24 in the desired position until flap adhesive cover 84 is removed. The second end portion 80B of the main wrapper sheet 80, along with the second end region 34 of sanitary napkin 20, and the tape tab 86 are then folded about the second fold axis F2. This places these components on top of the first end portion 80A of the main wrapper sheet 80 and the first end region 32 of sanitary napkin 20. By pressing the tape tab 86 onto the exterior of wrapper 78 in the position depicted in FIG. 4, the sanitary napkin 20, its flaps 24 and wrapper 78 remain in the configuration shown.

Preferably, to complete the individual packaging of the sanitary napkin 20 in the wrapper 78 of the present invention, each longitudinal side edge 80D of the main wrapper sheet 80 is then frangibly sealed after the sanitary napkin 20 and the wrapper 78 are in the folded configuration shown in FIG. 4A. The frangible sealing of the side edges 80D of the main wrapper sheet 80 can be accomplished by any suitable sealing technique. By way of example only, the longitudinal side edges 80D may be heat sealed, glued, or ultrasonically bonded. The entire sanitary napkin 20 is thereby protected until the wrapper 78 is opened. Suitable methods for frangibly sealing the longitudinal side edges are described in U.S. Pat. No. 4,556,146 issued to Swanson.

Figure 6:
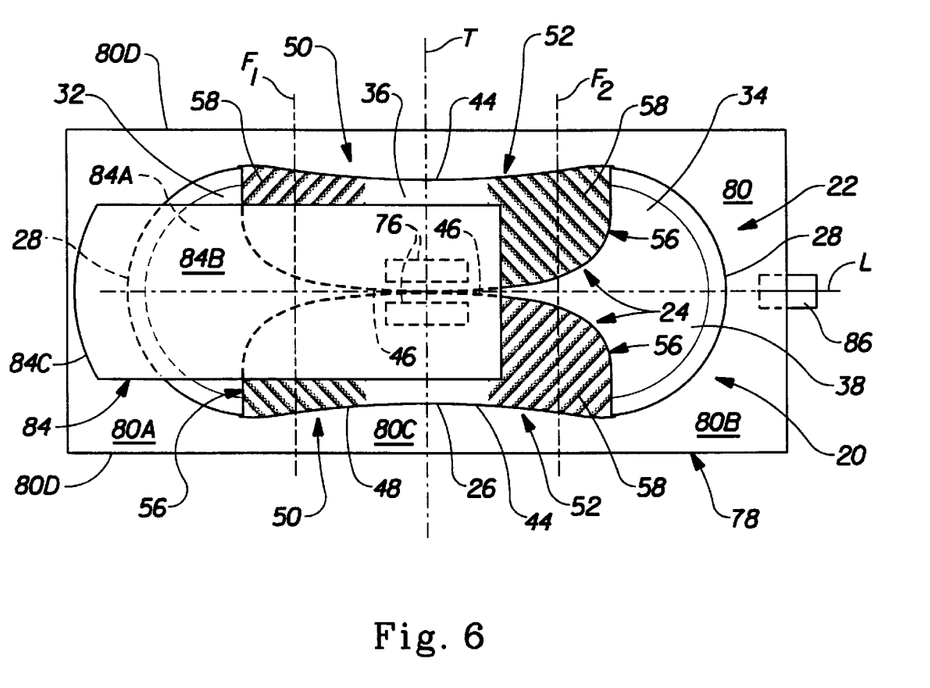
FIG. 6 is a top plan view of an alternative embodiment wrapper of the present invention with a sanitary napkin placed thereon in substantially the same configuration as FIG. 2.

Various alternative embodiments of the present invention are possible. For example in the embodiment shown in FIG. 6, instead of only extending over part of the first end region 32 of the sanitary napkin, flap adhesive cover 84 could be made longer so that it extends from one of the longitudinal ends of the main wrapper sheet 80 to overlie the central region 36 of the sanitary napkin 20 so that it covers the flap adhesives 76 when the wrapper 78 and sanitary napkin 20 are in an unfolded condition. In this embodiment, the non-stick side 84A of the flap adhesive cover 84 will face inward toward the main wrapper sheet 80, and the objectives of the invention will be accomplished regardless of the subsequent folded configuration of the wrapper 78 and napkin 20. Consequently, the wrapper 78 and sanitary napkin 20 could be folded upon themselves about the transverse centerline T, or in any other manner, to provide the individually packaged absorbent article of the present invention.

Figure 7:
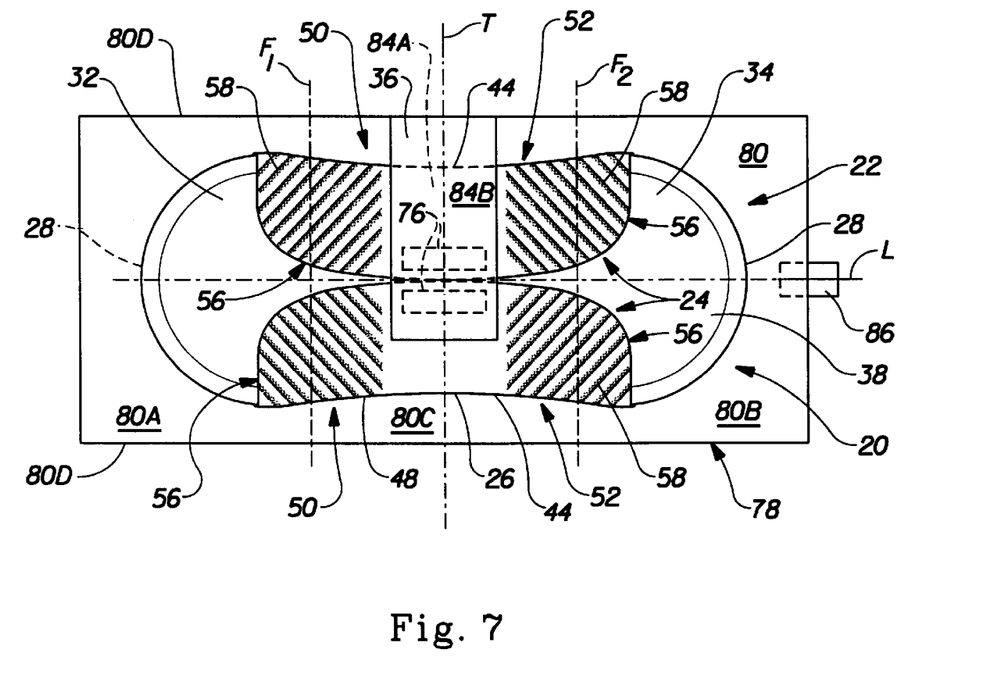
FIG. 7 is a top plan view of another alternative embodiment wrapper of the present invention with a sanitary napkin placed thereon in substantially the same configuration as FIG. 2.

In another, less preferred, alternative embodiment shown in FIG. 7, instead of being joined adjacent to one of the end edges of the main wrapper sheet 80, the flap adhesive cover 84 could be joined along one of the longitudinal edges 80D of the main wrapper sheet 80. In this embodiment, the flap adhesive cover 84 extends in the transverse direction over sanitary napkin 20 with the non-stick side 84A of the same facing toward the main wrapper sheet 80, and the flap adhesive cover 84 releasably attaching to the flap fasteners 76. In this embodiment, the objectives of the invention will also be accomplished regardless of the subsequent folded configuration of the wrapper 78 and napkin 20.

The various embodiments of the wrapper 78 described herein can be made in any suitable manner. The flap adhesive cover 84 may be made of the same material as the main wrapper sheet or any adhesive cover material known in the art. The flap adhesive cover 84, if a separate element, can be joined to the main wrapper sheet 80 at any time during the manufacture of the individually packaged sanitary napkin 20 of the present invention. Preferably, for ease of manufacture, the flap adhesive cover 84 will be joined to the main wrapper sheet 80 after the sanitary napkin 20 is already placed on the main wrapper sheet 80. This will eliminate the need to fold the flap adhesive cover 84 back as shown in FIG. 3A to allow the sanitary napkin 20 to be placed on the main wrapper sheet 80. The release paper or release coating 82 on the main wrapper sheet 80 and the non-stick surface 84A on the flap adhesive cover 84 can be applied either before or after the flap adhesive cover 84 is joined to the main wrapper sheet 80. Preferably, for ease of manufacture, these items are applied before the flap adhesive cover 84 is joined to the main wrapper sheet 80.

Figure 5:
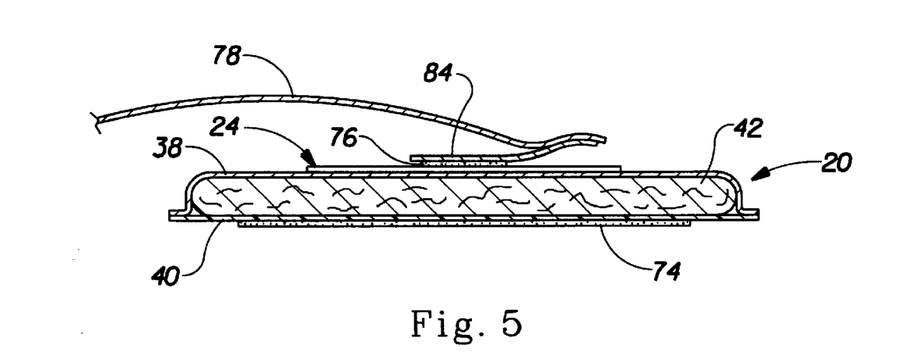
FIG. 5 is a cross-sectional view (taken along the longitudinal centerline) of one preferred wrapper of the present invention attached to a preferred sanitary napkin by the flap release element only.

The consumer will ordinarily carry the individually packaged sanitary napkin of the present invention in the form depicted in FIG. 4 and FIG. 4A. The individually packaged sanitary napkin of the present invention depicted in FIG. 4 and FIG. 4A may be opened by peeling tape tab 86 from the wrapper 78 and breaking the frangible seals along the longitudinal side edges 80D of the main wrapper sheet 80. The main wrapper sheet 80 may then be removed from the central pad fastener 74 on the sanitary napkin 20 by peeling the main wrapper sheet 80 from the central pad fastener 74. The consumer can peel away the wrapper 78 in the above manner and leave the flap adhesive cover 84 attached to each flap 24 by flap fasteners 76 as depicted in FIG. 5. If the consumer does this, the napkin may be placed in the crotch of the wearer's undergarment and secured thereto by central pad adhesive 74 while the flaps remain folded over the topsheet 38. More preferably, however, the consumer can peel the entire wrapper 78 from sanitary napkin 20 including the central pad adhesive fastener 74 and the flap adhesives 76 in a single motion. This can be accomplished after the consumer peels open the tape tab 86. This gives the consumer access to the end edge 28 at the second end region 34 of sanitary napkin 20. The consumer may then take hold of the end edge 28 at the second end region 34 of sanitary napkin 20 and pull the entirety of the wrapper 78 from the sanitary napkin 20 and its flaps 24 in a single motion.

Once the sanitary napkin is removed from the wrapper 78 and installed in the wearer's panties, the consumer may fold the wrapper 78, secure the wrapper 78 in its folded orientation by reattaching resealable tape tab 80 to wrapper 78. The consumer may then store the folded wrapper 78 for rewrapping and disposing of the used sanitary napkin. The wearer need not worry about collecting and disposing of loose flap adhesive release strips, that were previously required, since all release strips are attached to or integral with the wrapper 78. The present invention, therefore, provides the wearer with a clean sanitary napkin 20 which is easily installed and without extra pieces of waste which must be collected.

The disclosures of all patents, patent applications (and any patents which issue thereon, as well as any corresponding published foreign patent application), and publications mentioned throughout this description are hereby incorporated by reference herein. It is expressly not admitted, however, that any of the documents incorporated by reference herein teach or disclose the present invention.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An individually packaged absorbent article comprising:
   (a) an absorbent article comprising a main body portion having a pair of longitudinal side edges, a pair of end edges, a garment surface, and a body surface, wherein said garment surface of said main body portion may be placed in wearer's undergarment, and said absorbent article comprises a pair of flaps joined to said main body portion and extending laterally outward beyond a longitudinal side edge of said main body portion, wherein the garment surface of each of said flaps comprises a flap fastener and said flaps are folded over said body surface of said main body portion to expose said flap fasteners; and
   (b) a wrapper for said absorbent article, said wrapper comprising a main wrapper sheet and a flap fastener cover directly attached to said main wrapper sheet, wherein said main wrapper sheet is positioned adjacent to said garment surface of said main body portion, and said main wrapper sheet and said main body portion of said absorbent article are folded as a unit about at least one transverse axis and said flap fastener cover is releasably affixed to said flap fasteners.

2. The absorbent article of claim 1 wherein said flap fastener cover is an integral extension of said main wrapper sheet.

3. The absorbent article of claim 1 wherein said flap fastener cover comprises a separate element.

4. The absorbent article of claim 1 wherein said flap fastener is an adhesive and said flap fastener cover is provided with a nonstick surface for placement adjacent to said exposed flap fasteners.

5. The absorbent article of claim 1 wherein:

said main body portion of said absorbent article comprises a first end region, a second end region, and a central region positioned between said first end region and said second end region;

said main wrapper sheet comprises longitudinal edge portions which extend beyond the longitudinal side edges of the main body portion of said absorbent article and a first end portion located adjacent to said first end region of said main body portion and a second end portion located adjacent to said second end region of said main body portion, wherein at least said first end portion of said main wrapper sheet extends beyond the first end region of said main body portion of said absorbent article; and said flap fastener cover is joined to the first end portion of the main wrapper sheet and extends longitudinally therefrom to lie adjacent the body surface of said absorbent article in the first end region of the main body portion.

6. The absorbent article of claim 5 wherein said flap fastener cover only covers the first end region of the main body portion of the absorbent article when the main body portion is in an unfolded state, and the first end region of said main body portion of said absorbent article lies folded upon said central region of said absorbent article so that said flap fastener cover overlies and releasably covers said flap fasteners.

7. The absorbent article of claim 5 wherein said flap fastener cover also extends over and covers at least a portion of the body surface of said central region of said absorbent article and releasably covers said flap fasteners.

8. The absorbent article of claim 1 wherein the longitudinal edge portions of said main wrapper sheet are frangibly sealed together.

9. The absorbent article of claim 1 wherein:

said main body portion of said absorbent article comprises a first end region, a second end region, and a central region positioned between said first end region and said second end region;

said main wrapper sheet comprises longitudinal edge portions which extend beyond the longitudinal side edges of the main body portion of said absorbent article and a first end portion located adjacent to said first end region of said main body portion, a second end portion located adjacent to said second end region of said main body portion, and a central portion located adjacent to said central region of said absorbent article, wherein at least said first end portion of said main wrapper sheet extends beyond the first end region of said main body portion of said absorbent article; and said flap fastener cover is joined to the central portion of the main wrapper sheet adjacent one of the longitudinal edge portions thereof and extends transversely therefrom to overlie and releasably cover said flap fasteners.

10. An individually wrapped sanitary napkin comprising:

a napkin including an elongate napkin body having a liquid-permeable topsheet, a liquid-impermeable backsheet and a liquid-absorbent core disposed and encased therebetween, said napkin body further having longitudinally opposite end edges and transversely opposite side edges, and a pair of wings extending outward beyond the transversely opposite side edges of said napkin body, each wing having a top surface and a back surface;

a first release sheet releasably bonded onto an adhesive zone provided on said backsheet;

a second release sheet releasably bonded onto adhesive zones provided on the back surface of said wings which are folded along the transversely opposite side edges of said napkin body onto said topsheet;

an elongate wrapping sheet being fixedly bonded to an outer surface of said first release sheet so that longitudinally opposite end edges and transversely opposite side edges of said wrapping sheet extend outward beyond the longitudinally opposite end edges and the transversely opposite side edges of said napkin body respectively, said napkin and said wrapping sheet being folded with said topsheet lying inside and with a first longitudinal end of said napkin and said wrapping sheet underlying a second longitudinal end of said napkin and wrapping sheet, the transversely opposite side edges of said wrapping sheet being placed one upon another and sealed together; and wherein the longitudinal end edge of said wrapping sheet at the first longitudinal end edge of said napkin and said wrapping sheet is directly and fixedly bonded to said second release sheet.

11. An individually wrapped sanitary napkin according to claim 10, further comprising a tab having an adhesive inner surface which extends outward beyond the longitudinal end edge of said wrapping sheet at the second longitudinal end edge of said napkin and wrapping sheet, said tab being fixedly bonded to said longitudinal end edge of said wrapping sheet at the second longitudinal end edge of said napkin and wrapping sheet, the adhesive inner surface of said tab being releasably bonded onto an outer surface of a portion of said wrapping sheet to which said adhesive inner surface is opposed when the napkin and wrapping sheet are folded.

12. An individually wrapped sanitary napkin according to claim 10, wherein said wings are formed by bonding together portions of said topsheet and said backsheet which extend outward beyond the transversely opposite side edges of said napkin body.

* * * * *